United States Patent
Dumas et al.

(10) Patent No.: US 12,356,988 B2
(45) Date of Patent: Jul. 15, 2025

(54) PROCESS AND INTERMEDIATES FOR THE PREPARATION OF CERTAIN MESOIONIC PESTICIDES

(71) Applicant: CORTEVA AGRSCIENCE LLC, Indianapolis, IN (US)

(72) Inventors: Donald J. Dumas, Wilmington, DE (US); Junbae Hong, Newark, DE (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 1050 days.

(21) Appl. No.: 16/977,485

(22) PCT Filed: Mar. 4, 2019

(86) PCT No.: PCT/US2019/020478
§ 371 (c)(1),
(2) Date: Sep. 2, 2020

(87) PCT Pub. No.: WO2019/173173
PCT Pub. Date: Sep. 12, 2019

(65) Prior Publication Data
US 2021/0051958 A1  Feb. 25, 2021

Related U.S. Application Data

(60) Provisional application No. 62/638,493, filed on Mar. 5, 2018.

(51) Int. Cl.
*A01N 43/54* (2006.01)
*C07D 401/12* (2006.01)

(52) U.S. Cl.
CPC ........... *A01N 43/54* (2013.01); *C07D 401/12* (2013.01)

(58) Field of Classification Search
CPC .............................. A01N 43/54; C07D 401/12
See application file for complete search history.

(56) References Cited

U.S. PATENT DOCUMENTS

| 9,108,965 B2 | 8/2015 | Zhang |
| 2005/0113437 A1 | 5/2005 | McHardy et al. |

(Continued)

FOREIGN PATENT DOCUMENTS

| WO | 2005037790 A1 | 4/2005 |
| WO | 2007027385 A2 | 3/2007 |

(Continued)

OTHER PUBLICATIONS

Butula; Pharmazie 1978, 33, 428-430: Cheminform Abstract 1978, 9(49), 257. https://doi.org/10.1002/chin.197849257 (Year: 1978).*

(Continued)

Primary Examiner — Clinton A Brooks
Assistant Examiner — Josmalen M. Ramos-Lewis

(57) ABSTRACT

The present invention provides a method for preparing a compound of Formula B, Formula C, or Formula D:

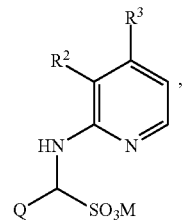

Formula B

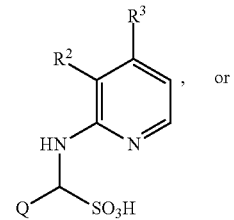

Formula C, or

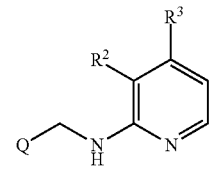

Formula D wherein Q is a 3- to 10-membered ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and such ring system is optionally substituted with up to 5 substituents independently selected from $R^4$;

each $R^4$ is independently halogen, hydroxy, $SF_5$, C(O)($C_1$-$C_8$ alkyl), C(O)O($C_1$-$C_8$ alkyl), N($C_1$-$C_8$ alkyl)($C_1$-$C_8$ alkyl), C(O)N($C_1$-$C_8$ alkyl)($C_1$-$C_8$ alkyl), C(=S)N($C_1$-$C_8$ alkyl)($C_1$-$C_8$ alkyl), $SO_2$N($C_1$-$C_8$ alkyl)($C_1$-$C_8$ alkyl), OC(O)($C_1$-$C_8$ alkyl), OC(O)O($C_1$-$C_8$ alkyl), OC(O)N($C_1$-$C_8$ alkyl)($C_1$-$C_8$ alkyl), N($C_1$-$C_8$ alkyl)C(O)O($C_1$-$C_8$ alkyl), N($C_1$-$C_8$ alkyl)C(O)N($C_1$-$C_8$ alkyl)($C_1$-$C_8$ alkyl), $OSO_2$($C_1$-$C_8$ alkyl), $OSO_2$N($C_1$-$C_8$ alkyl)($C_1$-$C_8$ alkyl), N($C_1$-$C_8$ alkyl)$SO_2$($C_1$-$C_8$ alkyl), or $C_1$-$C_8$ alkyl, $C_1$-$C_8$ haloalkyl, $C_2$-$C_8$ alkenyl, $C_2$-$C_8$ alkynyl, $C_3$-$C_{10}$ cycloalkyl, $C_3$-$C_{10}$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ (Continued)

cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl; or two $R^A$ substituents on adjacent ring atoms are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(O) and C(=S) and such ring is optionally substituted with up to 3 substituents independently selected from the group consisting of halogen, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl;

each of $R^2$ and $R^3$ is independently H, F, $C_1$-$C_4$ alkyl or $C_1$-$C_4$ haloalkyl; and M is an inorganic cation or organic cation.

1 Claim, No Drawings

(56) References Cited

U.S. PATENT DOCUMENTS

| | | | |
|---|---|---|---|
| 2007/0048217 | A1 | 3/2007 | McBride et al. |
| 2021/0051958 | A1 | 2/2021 | Dumas et al. |

FOREIGN PATENT DOCUMENTS

| | | |
|---|---|---|
| WO | 2009099929 A1 | 8/2009 |
| WO | 2013090547 A1 | 6/2013 |

OTHER PUBLICATIONS

Chemical Abstracts Stn Registry Database, record for RN 1854713-07-7, a-hydroxy-5-pyrimidinemethanesulfonic acid, sodium salt, Entered STN Jan. 28, 2016. (Year: 2016).*

Chemical Abstracts Stn Registry Database, record for RN 1854713-07-7. (Year: 2016).*

Berge SM, Bighley LD, Monkhouse DC. Pharmaceutical salts. J Pharm Sci. Jan. 1977;66(1):1-19. doi: 10.1002/jps.2600660104. (Year: 1977).*

Butula, et al., "Aminoalkane Sulfonic Acids. V. The Synthesis of Some Antimitotic N-Nitroso-?-Amino-2-Pyridyl- and-2-Pyrimidinylalkanesulfonic Acids," Acta Pharmaceutica Jugoslavica, Apr. 1, 1984, vol. 34, No. 4, pp. 233-240, ISSN 0001-6667, XP009527503.

Butula L., "Aminoalkane Sulfonic Acids. Synthesis of Some Mitodepressive Heterocyclic Aminoalkane Sulfonic Acids," Pharmazie, Jul. 1, 1978, vol. 33, No. 7, pp. 428-430, ISSN 0031-7144, XP009527505.

Chemical Abstracts Stn Registry Database, record for RN 1854713-07-7, a-hydroxy-5-pyrimidinemethanesulfonic acid, sodium salt, Entered STN Jan. 28, 2016.

Extended European Search Report for European Application No. 19763209.4, mailed May 31, 2021, 06 Pages.

Grygorenko O.O., et al., "Amino Sulfonic Acids, Peptidosulfonamides and Other Related Compounds", Tetrahedron, Feb. 20, 2018, vol. 74, pp. 1355-1421, XP085356227.

International Preliminary Report on Patentability for International Application No. PCT/US2019/020478, mailed Sep. 17, 2020, 10 Pages.

International Search Report and Written Opinion for International Application No. PCT/US2019/020478, mailed May 17, 2019, 12 Pages.

"Sodium;hydroxy(pyrimidin-5-yl)methanesulfonate | C5H5N2NaO4S," Database Accession No. 130923211, Pubchem Compound, Oct. 9, 2017, URL: NCBI, XP055637620.

Pandit C.R., et al., "Expedient Reductive Amination of Aldehyde Bisulfite Adducts," Synthesis, 2009, vol. 23, pp. 4032-4036, XP055637625.

* cited by examiner

PROCESS AND INTERMEDIATES FOR THE PREPARATION OF CERTAIN MESOIONIC PESTICIDES

CROSS REFERENCE TO RELATED APPLICATIONS

This application is a national phase entry of international patent application PCT/US19/20478 filed Mar. 4, 2019, which claims the benefit of U.S. Provisional Patent Application Ser. No. 62/638,493 filed Mar. 5, 2018, where both are expressly incorporated by reference herein.

BACKGROUND OF THE INVENTION

Mesoionic pesticides and methods for preparing them have been previously disclosed in, for example, WO 2009/099929, WO 2011/017334, WO 2011/017342, WO 2011/017347, WO 2012/092115, WO 2013/090547, and WO 2017/189339. In addition, N-[(5-pyrimidinyl)methyl]-2-pyridinamine has been previously disclosed as an important intermediate for preparing certain mesoionic pesticides. However, certain synthesis steps disclosed previously may not be suitable for large-scale manufacture. Thus there remains a need for alternative ways of preparing certain mesoionic pesticides.

SUMMARY OF THE INVENTION

In one aspect, the present invention provides a method for preparing a compound of Formula B, Formula C, or Formula D:

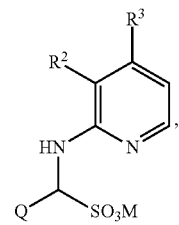

Formula B

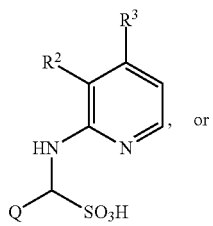

Formula C, or

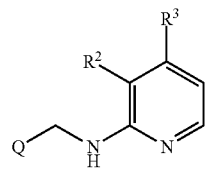

Formula D wherein Q is a 3- to 10-membered ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and such ring system is optionally substituted with up to 5 substituents independently selected from $R^4$;

each $R^4$ is independently halogen, hydroxy, $SF_5$, C(O)($C_1$-$C_8$ alkyl), C(O)O($C_1$-$C_8$ alkyl), N($C_1$-$C_8$ alkyl)($C_1$-$C_8$ alkyl), C(O)N($C_1$-$C_8$ alkyl)($C_1$-$C_8$ alkyl), C(=S)N($C_1$-$C_8$ alkyl)($C_1$-$C_8$ alkyl), $SO_2$N($C_1$-$C_8$ alkyl)($C_1$-$C_8$ alkyl), OC(O)($C_1$-$C_8$ alkyl), OC(O)O($C_1$-$C_8$ alkyl), OC(O)N($C_1$-$C_8$ alkyl)($C_1$-$C_8$ alkyl), N($C_1$-$C_8$ alkyl)C(O)O($C_1$-$C_8$ alkyl), N($C_1$-$C_8$ alkyl)C(O)N($C_1$-$C_8$ alkyl)($C_1$-$C_8$ alkyl), $OSO_2$($C_1$-$C_8$ alkyl), $OSO_2$N($C_1$-$C_8$ alkyl)($C_1$-$C_8$ alkyl), N($C_1$-$C_8$ alkyl)$SO_2$($C_1$-$C_8$ alkyl), or $C_1$-$C_8$ alkyl, $C_1$-$C_8$ haloalkyl, $C_2$-$C_8$ alkenyl, $C_2$-$C_8$ alkynyl, $C_3$-$C_{10}$ cycloalkyl, $C_3$-$C_{10}$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl; or two $R^4$ substituents on adjacent ring atoms are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(O) and C(=S) and such ring is optionally substituted with up to 3 substituents independently selected from the group consisting of halogen, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ haloalkylcycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl;

each of $R^2$ and $R^3$ is independently H, F, $C_1$-$C_4$ alkyl or $C_1$-$C_4$ haloalkyl; and M is an inorganic cation or organic cation;

comprising:

(a) contacting a compound of Formula A

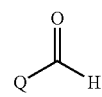

Formula A with a compound of Formula J

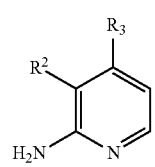

Formula J and a salt comprising at least one bisulfite salt, at least one metabisulfite salt, or mixtures thereof to form a compound of Formula B Formula B

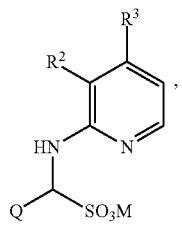

wherein M is at least one inorganic cation, at least one organic cation, or mixtures thereof derived from the salt; and optionally a compound of Formula C can be synthesized by contacting a compound of Formula B with an acid comprising at least one inorganic acid, at least one organic acid, or mixtures thereof Formula C

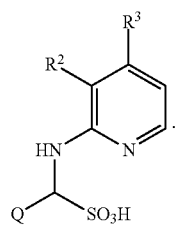

In some embodiments, $R^2$ is H or F. In some embodiments, $R^3$ is H or F.

In some embodiments, Q is triazolyl, pyridinyl, or pyrimidinyl, each optionally substituted with up to 2 substitutions independently selected from the group consisting of halogen, $C_1$-$C_8$ alkyl, $C_1$-$C_8$ haloalkyl, $C_3$-$C_{10}$ cycloalkyl, $C_3$-$C_{10}$ halocycloalkyl, $C_1$-$C_8$ alkoxy, $C_1$-$C_8$ haloalkoxy, $C_3$-$C_8$ cycloalkoxy, $C_3$-$C_8$ halocycloalkoxy, and $C_4$-$C_{10}$ cycloalkylalkoxy.

In other embodiments, Q is selected from one of the following ring structures:

Q1

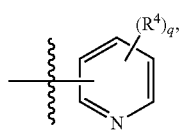

Q2

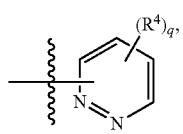

Q3

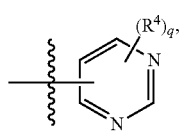

Q4

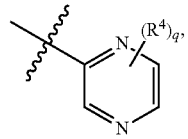

Q5

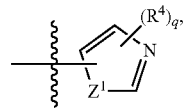

Q6

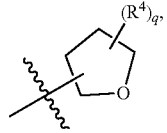

Q7

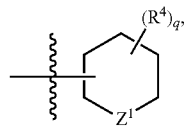

Q8

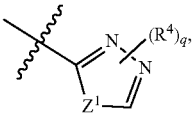

Q9

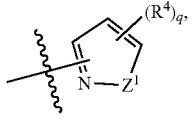

Q10

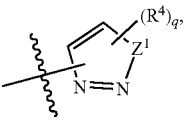

Q11

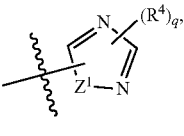

Q12

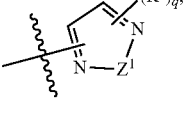

Q13

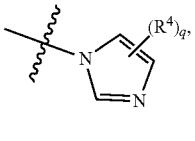

Q14

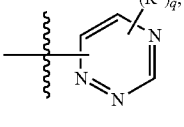

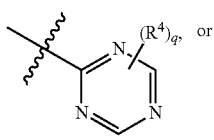

Q15

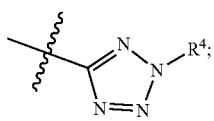

Q16 wherein $Z^1$ is O, S, or $NR^5$;

each $R^4$ or $R^5$ is independently H, halogen, hydroxy, $SF_5$, $C(O)(C_1-C_8$ alkyl), $C(O)O(C_1-C_8$ alkyl), $N(C_1-C_8$ alkyl)$(C_1-C_8$ alkyl), $C(O)N(C_1-C_8$ alkyl)$(C_1-C_8$ alkyl), $C(=S)N(C_1-C_8$ alkyl)$(C_1-C_8$ alkyl), $SO_2N(C_1-C_8$ alkyl)$(C_1-C_8$ alkyl), $OC(O)(C_1-C_8$ alkyl), $OC(O)O(C_1-C_8$ alkyl), $OC(O)N(C_1-C_8$ alkyl)$(C_1-C_8$ alkyl), $N(C_1-C_8$ alkyl)$C(O)O(C_1-C_8$ alkyl), $N(C_1-C_8$ alkyl)$C(O)N(C_1-C_8$ alkyl)$(C_1-C_8$ alkyl), $OSO_2(C_1-C_8$ alkyl), $OSO_2N(C_1-C_8$ alkyl)$(C_1-C_8$ alkyl), $N(C_1-C_8$ alkyl)$SO_2(C_1-C_8$ alkyl), or $C_1-C_8$ alkyl, $C_1-C_8$ haloalkyl, $C_2-C_8$ alkenyl, $C_2-C_8$ alkynyl, $C_3-C_{10}$ cycloalkyl, $C_3-C_{10}$ halocycloalkyl, $C_4-C_{10}$ alkylcycloalkyl, $C_4-C_{10}$ cycloalkylalkyl, $C_6-C_{14}$ cycloalkylcycloalkyl, $C_5-C_{10}$ alkylcycloalkylalkyl, $C_3-C_8$ cycloalkenyl, $C_1-C_8$ alkoxy, $C_1-C_8$ haloalkoxy, $C_3-C_8$ cycloalkoxy, $C_3-C_8$ halocycloalkoxy, $C_4-C_{10}$ cycloalkylalkoxy, $C_2-C_8$ alkenyloxy, $C_2-C_8$ alkynyloxy, $C_1-C_8$ alkylthio, $C_1-C_8$ alkylsulfinyl, $C_1-C_8$ alkylsulfonyl, $C_3-C_8$ cycloalkylthio, $C_3-C_8$ cycloalkylsulfinyl, $C_3-C_8$ cycloalkylsulfonyl, $C_4-C_{10}$ cycloalkylalkylthio, $C_4-C_{10}$ cycloalkylalkylsulfinyl, $C_4-C_{10}$ cycloalkylalkylsulfonyl, $C_2-C_8$ alkenylthio, $C_2-C_8$ alkenylsulfinyl, $C_2-C_8$ alkenylsulfonyl, $C_2-C_8$ alkynylthio, $C_2-C_8$ alkynylsulfinyl or $C_2-C_8$ alkynylsulfonyl; and each q is independently 0, 1, or 2.

In some embodiments, the salt comprises sodium bisulfite, potassium bisulfite, ammonium bisulfite, trimethylammonium bisulfite, triethylammonium bisulfite, sodium metabisulfite, potassium metabisulfite, ammonium metabisulfite, trimethylammonium metabisulfite, triethylammonium metabisulfite, or mixtures thereof. In some further embodiments, M is sodium, potassium, ammonium, trimethylammonium, triethylammonium, lithium, or mixtures thereof. In some embodiments, Step (a) is performed in the presence of a solvent comprising water, $C_1-C_4$ monohydric alcohol, $C_2-C_6$ polyhydric alcohol, or mixtures thereof.

In some embodiments, the methods provided further comprise Step (b) to prepare a compound of Formula C:

(b) contacting the compound of Formula B from Step (a) with an acid selected from at least one inorganic acid, at least one organic acid, or mixtures thereof to form a compound of Formula C:

Formula C

In some further embodiments, the acid comprises an inorganic acid selected from hydrochloric acid (HCl), hydrobromic acid (HBr), phosphoric acid ($H_3PO_4$), sulfuric acid ($H_2SO_4$), and boric acid ($H_3BO_3$). In some further embodiments, the acid comprises an organic acid selected from formic acid, acetic acid, propionic acid, citric acid, malic acid, and sulfonic acids. Examples of sulfonic acids including para-toluenesulfonic acid, methanesulfonic acid, and toluenesulfonic acid as a mixture of isomers.

In some embodiments, the methods provided further comprise Step (c) to prepare a compound of Formula D:

(c) contacting the compound of Formula B from Step (a) or the compound of Formula C from Step (b) with a reducing agent to form the compound of Formula D Formula D In some further embodiments, the reducing agent comprises a borohydride reducing agent selected from sodium borohydride ($NaBH_4$), sodium triacetoxyborohydride ($NaBH(CH_3COO)_3$), lithium borohydride ($LiBH_4$), potassium borohydride ($KBH_4$), sodium cyanoborohydride ($NaB(CN)H_3$), tetramethylammonium borohydride $((CH_3)_4NBH_4)$, tetraethylammonium borohydride $((C_2H_5)_4NBH_4)$, borane ($BH_3$), diborane ($B_2H_6$), bis-3-methyl-2-butylborane $([(CH_3)_2CHCH(CH_3)]2BH)$ or mixtures thereof. In some further embodiments, the reducing agent comprises lithium aluminium hydride ($LiAlH_4$), diisobutylaluminium hydride (DIBALH), lithium tri-tert-butoxyaluminum hydride ($LiAlH[OC(CH_3)_3]_3$), lithium tri-methoxyaluminum hydride ($LiAlH(OCH_3)_3$), or mixtures thereof. In some embodiments, the reducing agent comprises hydrogen in conjunction with a metal catalyst including, for example, Raney nickel, supported palladium, supported platinum, or mixtures thereof.

In some embodiments, the invention provides a method for preparing a compound of Formula 1

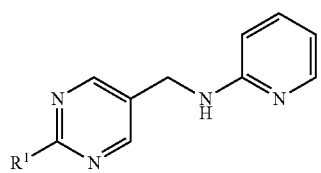

Formula 1 wherein $R^1$ is H or $C_1-C_3$ alkyl, comprising:
(A) contacting a compound of Formula 2 or Formula 2a

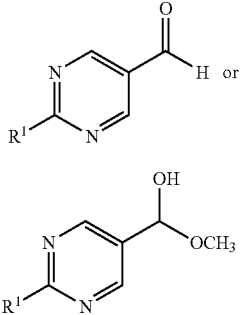

Formula 2

Formula 2a with 2-aminopyridine (3)

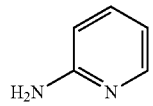

Formula 3 and a salt consisting of a bisulfite salt, a metabisulfite salt, or a mixture of a bisulfite salt and a metabisulfite salt in the presence of a solvent S1 to form a compound of Formula 4

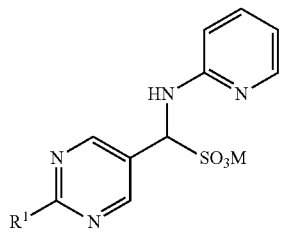

Formula 4 wherein $R^1$ is H or $C_1$-$C_3$ alkyl and M is an inorganic or organic cation;
(B) contacting the compound of Formula 4 with an inorganic or organic acid in the presence of a solvent S2 to form a compound of Formula 5

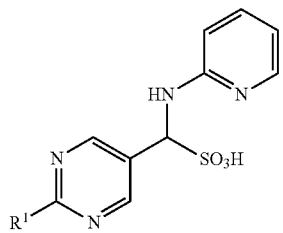

Formula 5 wherein $R^1$ is H or $C_1$-$C_3$ alkyl; and
(C) contacting the compound of Formula 4 or Formula 5 with a borohydride reducing agent in the presence of an inorganic or organic base and a solvent S3 to form the compound of Formula 1.

In some further embodiments, Step (C) further comprises
(i) contacting the reaction mixture with water and adjusting the pH of the reaction mixture with acid to pH less than 5,
(ii) separating resulting aqueous and organic phases of the reaction mixture,
(iii) adjusting the pH of the aqueous phase to pH 5 or greater with aqueous base, and
(iv) extracting the compound of Formula 1 into an organic solvent selected from $C_7$-$C_{10}$ aromatic hydrocarbons, haloalkanes, halogenated benzenes, $C_5$-$C_{10}$ aliphatic hydrocarbons, and $C_5$-$C_{10}$ cycloaliphatic hydrocarbons.

In some further embodiments, the organic solvent of Step (iv) is toluene, dichloromethane, 1,2-dichloroethane or 1-chlorobutane.

In another aspect, the present invention provides a method for preparing a compound of Formula B, Formula C, or Formula D:

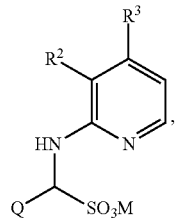

Formula B

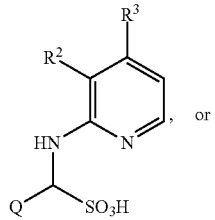

Formula C

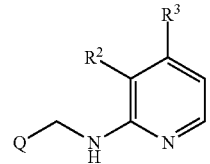

Formula D wherein Q is a 3- to 10-membered ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and such ring system is optionally substituted with up to 5 substituents independently selected from $R^A$;
each $R^A$ is independently halogen, hydroxy, $SF_5$, C(O)($C_1$-$C_8$ alkyl), C(O)O($C_1$-$C_8$ alkyl), N($C_1$-$C_8$ alkyl)($C_1$-$C_8$ alkyl), C(O)N($C_1$-$C_8$ alkyl)($C_1$-$C_8$ alkyl), C(=S)N($C_1$-$C_8$ alkyl)($C_1$-$C_8$ alkyl), $SO_2$N($C_1$-$C_8$ alkyl)($C_1$-$C_8$ alkyl), OC(O)($C_1$-$C_8$ alkyl), OC(O)O($C_1$-$C_8$ alkyl), OC(O)N($C_1$-$C_8$ alkyl)($C_1$-$C_8$ alkyl), N($C_1$-$C_8$ alkyl)C(O)O($C_1$-$C_8$ alkyl), N($C_1$-$C_8$ alkyl)C(O)N($C_1$-$C_8$ alkyl)($C_1$-$C_8$ alkyl), $OSO_2$($C_1$-$C_8$ alkyl), $OSO_2$N($C_1$-$C_8$ alkyl)($C_1$-$C_8$ alkyl), N($C_1$-$C_8$ alkyl)$SO_2$($C_1$-$C_8$ alkyl), or $C_1$-$C_8$ alkyl, $C_1$-$C_8$ haloalkyl, $C_2$-$C_8$ alkenyl, $C_2$-$C_8$ alkynyl, $C_3$-$C_{10}$ cycloalkyl, $C_3$-$C_{10}$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl; or two $R^4$ substituents on adjacent ring atoms are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(O) and C(=S) and such ring is optionally substituted with up to 3 substituents independently selected from the group consisting of halogen, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl;

each of $R^2$ and $R^3$ is independently H, F, $C_1$-$C_4$ alkyl or $C_1$-$C_4$ haloalkyl; and M is an inorganic cation or organic cation;

comprising:

(a) contacting a compound of Formula A

Formula A with a salt comprising at least one bisulfate salt, at least one metabisulfite salt, or mixtures thereof to form a compound of Formula E

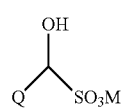

Formula E wherein M is at least one inorganic cation, at least one organic cation, or mixtures thereof derived from the salt; and (b) contacting the compound of Formula E from Step (a) with a compound of Formula J to form a compound of Formula B

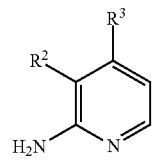

Formula J

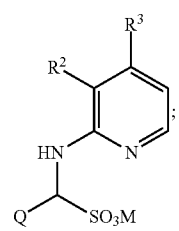

Formula B optionally a compound of Formula C can be synthesized by contacting a compound of Formula B with an acid comprising at least one inorganic acid, at least one organic acid, or mixtures thereof

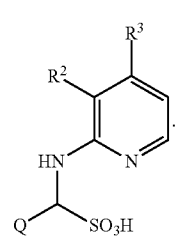

Formula C

In some embodiments, $R^2$ is H or F. In some embodiments, $R^3$ is H or F.

In some embodiments, Q is triazolyl, pyridinyl, or pyrimidinyl, each optionally substituted with up to 2 substitutions independently selected from the group consisting of halogen, $C_1$-$C_8$ alkyl, $C_1$-$C_8$ haloalkyl, $C_3$-$C_{10}$ cycloalkyl, $C_3$-$C_{10}$ halocycloalkyl, $C_1$-$C_8$ alkoxy, $C_1$-$C_8$ haloalkoxy, $C_3$-$C_8$ cycloalkoxy, $C_3$-$C_8$ halocycloalkoxy, and $C_4$-$C_{10}$ cycloalkylalkoxy.

In other embodiments, Q is selected from one of the following ring structures:

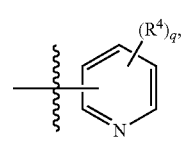

Q1

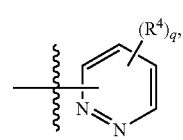

Q2

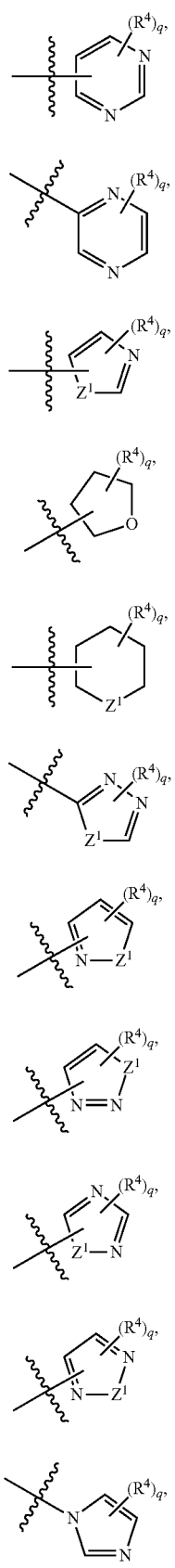

wherein $Z^1$ is O, S, or $NR^5$;

each $R^4$ or $R^5$ is independently H, halogen, hydroxy, $SF_5$, $C(O)(C_1-C_8$ alkyl), $C(O)O(C_1-C_8$ alkyl), $N(C_1-C_8$ alkyl)($C_1-C_8$ alkyl), $C(O)N(C_1-C_8$ alkyl)($C_1-C_8$ alkyl), $C(=S)N(C_1-C_8$ alkyl)($C_1-C_8$ alkyl), $SO_2N(C_1-C_8$ alkyl)($C_1-C_8$ alkyl), $OC(O)(C_1-C_8$ alkyl), $OC(O)O(C_1-C_8$ alkyl), $OC(O)N(C_1-C_8$ alkyl)($C_1-C_8$ alkyl), $N(C_1-C_8$ alkyl)$C(O)O(C_1-C_8$ alkyl), $N(C_1-C_8$ alkyl)$C(O)N(C_1-C_8$ alkyl)($C_1-C_8$ alkyl), $OSO_2(C_1-C_8$ alkyl), $OSO_2N(C_1-C_8$ alkyl)($C_1-C_8$ alkyl), $N(C_1-C_8$ alkyl)$SO_2(C_1-C_8$ alkyl), or $C_1-C_8$ alkyl, $C_1-C_8$ haloalkyl, $C_2-C_8$ alkenyl, $C_2-C_8$ alkynyl, $C_3-C_{10}$ cycloalkyl, $C_3-C_{10}$ halocycloalkyl, $C_4-C_{10}$ alkylcycloalkyl, $C_4-C_{10}$ cycloalkylalkyl, $C_6-C_{14}$ cycloalkylcycloalkyl, $C_5-C_{10}$ alkylcycloalkylalkyl, $C_3-C_8$ cycloalkenyl, $C_1-C_8$ alkoxy, $C_1-C_8$ haloalkoxy, $C_3-C_8$ cycloalkoxy, $C_3-C_8$ halocycloalkoxy, $C_4-C_{10}$ cycloalkylalkoxy, $C_2-C_8$ alkenyloxy, $C_2-C_8$ alkynyloxy, $C_1-C_8$ alkylthio, $C_1-C_8$ alkylsulfinyl, $C_1-C_8$ alkylsulfonyl, $C_3-C_8$ cycloalkylthio, $C_3-C_8$ cycloalkylsulfinyl, $C_3-C_8$ cycloalkylsulfonyl, $C_4-C_{10}$ cycloalkylalkylthio, $C_4-C_{10}$ cycloalkylalkylsulfinyl, $C_4-C_{10}$ cycloalkylalkylsulfonyl, $C_2-C_8$ alkenylthio, $C_2-C_8$ alkenylsulfinyl, $C_2-C_8$ alkenylsulfonyl, $C_2-C_8$ alkynylthio, $C_2-C_8$ alkynylsulfinyl or $C_2-C_8$ alkynylsulfonyl; and each q is independently 0, 1, or 2.

In some embodiments, the salt comprises sodium bisulfite, potassium bisulfite, ammonium bisulfite, trimethylammonium bisulfite, triethylammonium bisulfite, sodium metabisulfite, potassium metabisulfite, ammonium metabisulfite, trimethylammonium metabisulfite, triethylammonium metabisulfite, or mixtures thereof. In some further embodiments, M is sodium, potassium, ammonium, trimethylammonium, triethylammonium, lithium, or mixtures thereof. In some embodiments, Step (a) is performed in the presence of a solvent comprising water, $C_1-C_4$ monohydric alcohol, $C_2-C_6$ polyhydric alcohol, or mixtures thereof.

In some embodiments, the methods provided further comprise Step (c) to prepare a compound of Formula C:

(c) contacting the compound of Formula B from Step (b) with an acid selected from at least one inorganic acid, at least one organic acid, or mixtures thereof to form a compound of Formula C:

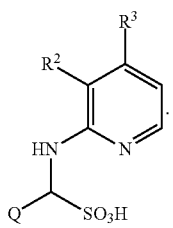

Formula C

In some further embodiments, the acid comprises an inorganic acid selected from hydrochloric acid (HCl), hydrobromic acid (HBr), phosphoric acid ($H_3PO_4$), sulfuric acid ($H_2SO_4$), and boric acid ($H_3BO_3$). In some further embodiments, the acid comprises an organic acid selected from formic acid, acetic acid, propionic acid, citric acid, malic acid, and sulfonic acids. Examples of sulfonic acids including para-toluenesulfonic acid, methanesulfonic acid, and toluenesulfonic acid as a mixture of isomers.

In some embodiments, the methods provided further comprise Step (d) to prepare a compound of Formula D:
(d) contacting the compound of Formula B from Step (b) or of Formula C from Step (c) with a reducing agent to form the compound of Formula D

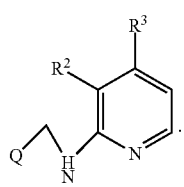

Formula D

In some further embodiments, the reducing agent comprises a borohydride reducing agent selected from sodium borohydride ($NaBH_4$), sodium triacetoxyborohydride ($NaBH(CH_3COO)_3$), lithium borohydride ($LiBH_4$), potassium borohydride ($KBH_4$), sodium cyanoborohydride ($NaB(CN)H_3$), tetramethylammonium borohydride (($CH_3$)$_4NBH_4$), tetraethylammonium borohydride (($C_2H_5$)$_4NBH_4$), borane ($BH_3$), diborane ($B_2H_6$), bis-3-methyl-2-butylborane ($[(CH_3)_2CHCH(CH_3)]2BH$) or mixtures thereof. In some further embodiments, the reducing agent comprises lithium aluminium hydride ($LiAlH_4$), diisobutylaluminium hydride (DIBALH), lithium tri-tert-butoxyaluminum hydride ($LiAlH[OC(CH_3)_3]_3$), lithium tri-methoxyaluminum hydride ($LiAlH(OCH_3)_3$), or mixtures thereof. In some embodiments, the reducing agent comprises hydrogen in conjunction with a metal catalyst including, for example, Raney nickel, supported palladium, supported platinum, or mixtures thereof.

In some embodiments, the invention provides a method for preparing a compound of Formula 1

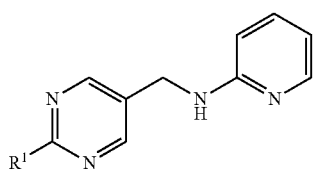

Formula 1 wherein $R^1$ is H or $C_1$-$C_3$ alkyl, comprising:

(A) contacting a compound of Formula 2 or Formula 2a

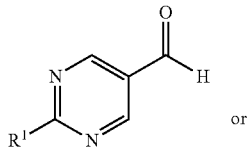

Formula 2 or

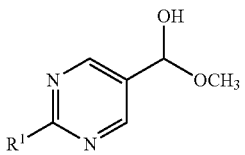

Formula 2a with a salt consisting of a bisulfite salt, a metabisulfite salt, or a mixture of a bisulfite salt and a metabisulfite salt in the presence of a solvent S1 to form a compound of Formula 6

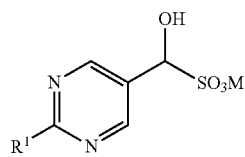

Formula 6 wherein $R^1$ is H or $C_1$-$C_3$ alkyl and M is an inorganic or organic cation;

(B) contacting the compound of Formula 6 with 2-aminopyridine (3)

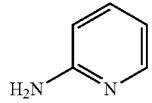

Formula 3 in the presence of a solvent S1A (for example consisting of water or a mixture of water and an alcohol) to form a compound of Formula 4

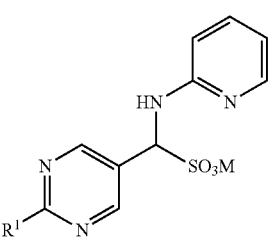

Formula 4 wherein $R^1$ is H or $C_1$-$C_3$ alkyl and M is an inorganic or organic cation;

(C) contacting the compound of Formula 4 with an inorganic or organic acid in the presence of a solvent S2 to form a compound of Formula 5

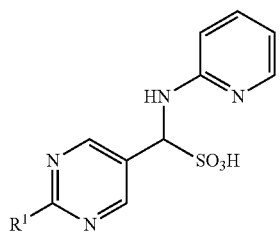

Formula 5 wherein R¹ is H or $C_1$-$C_3$ alkyl; and (D) contacting the compound of Formula 4 or Formula 5 with a borohydride reducing agent in the optional presence of an inorganic or organic base and a solvent S3 to form the compound of Formula 1.

In another aspect, the invention also provides a method for preparing a compound of Formula F

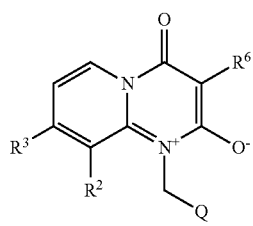

Formula F wherein Q is a 3- to 10-membered ring system containing ring members selected from carbon atoms and up to 4 heteroatoms independently selected from up to 2 O, up to 2 S, and up to 4 N, wherein up to 3 carbon atom ring members are independently selected from C(=O) and C(=S) and such ring system is optionally substituted with up to 5 substituents independently selected from $R^A$;

each $R^A$ is independently halogen, hydroxy, $SF_5$, C(O)($C_1$-$C_8$ alkyl), C(O)O($C_1$-$C_8$ alkyl), N($C_1$-$C_8$ alkyl)($C_1$-$C_8$ alkyl), C(O)N($C_1$-$C_8$ alkyl)($C_1$-$C_8$ alkyl), C(=S)N($C_1$-$C_8$ alkyl)($C_1$-$C_8$ alkyl), $SO_2$N($C_1$-$C_8$ alkyl)($C_1$-$C_8$ alkyl), OC(O)($C_1$-$C_8$ alkyl), OC(O)O($C_1$-$C_8$ alkyl), OC(O)N($C_1$-$C_8$ alkyl)($C_1$-$C_8$ alkyl), N($C_1$-$C_8$ alkyl)C(O)O($C_1$-$C_8$ alkyl), N($C_1$-$C_8$ alkyl)C(O)N($C_1$-$C_8$ alkyl)($C_1$-$C_8$ alkyl), $OSO_2$($C_1$-$C_8$ alkyl), $OSO_2$N($C_1$-$C_8$ alkyl)($C_1$-$C_8$ alkyl), N($C_1$-$C_8$ alkyl)$SO_2$($C_1$-$C_8$ alkyl), or $C_1$-$C_8$ alkyl, $C_1$-$C_8$ haloalkyl, $C_2$-$C_8$ alkenyl, $C_2$-$C_8$ alkynyl, $C_3$-$C_{10}$ cycloalkyl, $C_3$-$C_{10}$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl; or two $R^A$ substituents on adjacent ring atoms are taken together to form a 5- to 7-membered carbocyclic or heterocyclic ring, each ring containing ring members selected from carbon atoms and up to 3 heteroatoms independently selected from up to 2 O, up to 2 S, and up to 3 N, wherein up to 2 carbon atom ring members are independently selected from C(O) and C(=S) and such ring is optionally substituted with up to 3 substituents independently selected from the group consisting of halogen, hydroxy, $C_1$-$C_4$ alkyl, $C_1$-$C_4$ haloalkyl, $C_2$-$C_4$ alkenyl, $C_2$-$C_4$ haloalkenyl, $C_2$-$C_4$ alkynyl, $C_2$-$C_4$ haloalkynyl, $C_3$-$C_7$ cycloalkyl, $C_3$-$C_7$ halocycloalkyl, $C_4$-$C_8$ alkylcycloalkyl, $C_4$-$C_8$ haloalkylcycloalkyl, $C_4$-$C_8$ cycloalkylalkyl, $C_4$-$C_8$ halocycloalkylalkyl, $C_1$-$C_8$ alkoxy, $C_1$-$C_8$ haloalkoxy, $C_2$-$C_8$ alkoxycarbonyl, $C_2$-$C_6$ haloalkoxycarbonyl, $C_2$-$C_6$ alkylcarbonyl and $C_2$-$C_6$ haloalkylcarbonyl;

each of $R^2$ and $R^3$ is independently H, F, $C_1$-$C_4$ alkyl or $C_1$-$C_4$ haloalkyl; and $R^6$ is phenyl or pyridinyl, each optionally substituted with up to 3 substituents independently selected from phenyl, pyridinyl, halogen, $C_1$-$C_8$ alkyl, $C_1$-$C_8$ haloalkyl, $C_1$-$C_8$ alkoxy, $C_1$-$C_8$ haloalkoxy, $C_3$-$C_8$ cycloalkyl, $C_3$-$C_8$ halocycloalkyl, $C_1$-$C_8$ alkylthio or $C_1$-$C_8$ haloalkylthio;

comprising:

(a) contacting a compound of Formula G with a compound of Formula B, Formula C, or Formula D to produce a compound of Formula H:

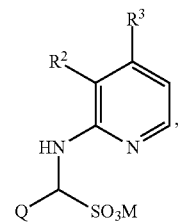

Formula G wherein X is Cl or Br,

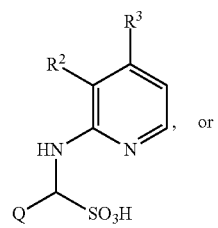

Formula B

, or

Formula C

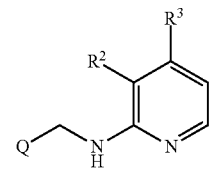

Formula D wherein M comprises at least one inorganic cation, at least one organic cation, or mixtures thereof,

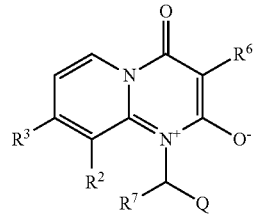

Formula H wherein $R^7$ is $SO_3M$, $SO_3H$, or H depending on whether a compound of Formula B, Formula C, or Formula D is used; and
(b) contacting the compound of Formula H from Step (a) with a reducing agent to form the compound of Formula F if $R^7$ is $SO_3M$ or $SO_3H$.

In some embodiments, $R^2$ is H or F. In some embodiments, $R^3$ is H or F.

In some embodiments, Q is triazolyl, pyridinyl, or pyrimidinyl, each optionally substituted with up to 2 substitutions independently selected from the group consisting of halogen, $C_1$-$C_8$ alkyl, $C_1$-$C_8$ haloalkyl, $C_3$-$C_{10}$ cycloalkyl, $C_3$-$C_{10}$ halocycloalkyl, $C_1$-$C_8$ alkoxy, $C_1$-$C_8$ haloalkoxy, $C_3$-$C_8$ cycloalkoxy, $C_3$-$C_8$ halocycloalkoxy, and $C_4$-$C_{10}$ cycloalkylalkoxy.

In other embodiments, Q is selected from one of the following ring structures:

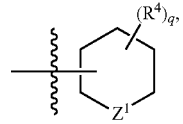 Q1

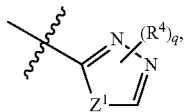 Q2

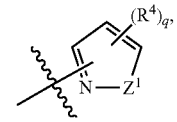 Q3

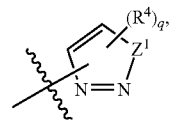 Q4

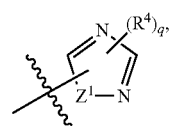 Q5

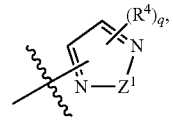 Q6

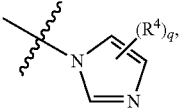 Q7

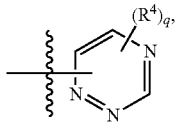 Q8

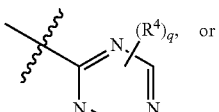 Q9

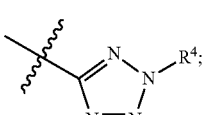 Q10

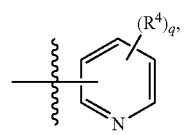 Q11

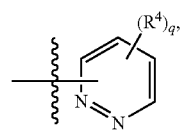 Q12

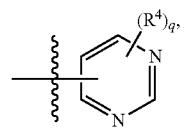 Q13

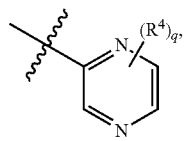 Q14

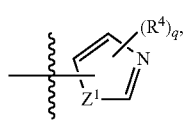 Q15

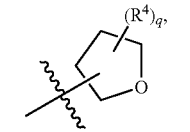 Q16 wherein $Z^1$ is O, S, or $NR^5$;
each $R^4$ or $R^5$ is independently H, halogen, hydroxy, $SF_5$, $C(O)(C_1$-$C_8$ alkyl), $C(O)O(C_1$-$C_8$ alkyl), $N(C_1$-$C_8$ alkyl)($C_1$-$C_8$ alkyl), $C(O)N(C_1$-$C_8$ alkyl)($C_1$-$C_8$ alkyl), $C(=S)N(C_1$-$C_8$ alkyl)($C_1$-$C_8$ alkyl), $SO_2N(C_1$-$C_8$ alkyl)($C_1$-$C_8$ alkyl), $OC(O)(C_1$-$C_8$ alkyl), $OC(O)O(C_1$-$C_8$ alkyl), $OC(O)N(C_1$-$C_8$ alkyl)($C_1$-$C_8$ alkyl), $N(C_1$-$C_8$ alkyl)$C(O)O(C_1$-$C_8$ alkyl), $N(C_1$-$C_8$ alkyl)$C(O)N(C_1$-$C_8$ alkyl)($C_1$-$C_8$ alkyl), $OSO_2(C_1$-$C_8$ alkyl), $OSO_2N(C_1$-$C_8$ alkyl)($C_1$-$C_8$ alkyl), $N(C_1$-$C_8$ alkyl)$SO_2(C_1$-$C_8$ alkyl), or $C_1$-$C_8$ alkyl, $C_1$-$C_8$ haloalkyl, $C_2$-$C_8$ alkenyl, $C_2$-$C_8$ alkynyl, $C_3$-$C_{10}$ cycloalkyl, $C_3$-$C_{10}$ halocycloalkyl, $C_4$-$C_{10}$ alkylcycloalkyl, $C_4$-$C_{10}$ cycloalkylalkyl, $C_6$-$C_{14}$ cycloalkylcycloalkyl, $C_5$-$C_{10}$ alkylcycloalkylalkyl, $C_3$-$C_8$ cycloalkenyl, $C_1$-$C_8$ alkoxy, $C_1$-$C_8$ haloalkoxy, $C_3$-$C_8$ cycloalkoxy, $C_3$-$C_8$ halocycloalkoxy, $C_4$-$C_{10}$ cycloalkylalkoxy, $C_2$-$C_8$ alkenyloxy, $C_2$-$C_8$ alkynyloxy, $C_1$-$C_8$ alkylthio, $C_1$-$C_8$ alkylsulfinyl, $C_1$-$C_8$ alkylsulfonyl, $C_3$-$C_8$ cycloalkylthio, $C_3$-$C_8$ cycloalkylsulfinyl, $C_3$-$C_8$ cycloalkylsulfonyl, $C_4$-$C_{10}$ cycloalkylalkylthio, $C_4$-$C_{10}$ cycloalkylalkylsulfinyl, $C_4$-$C_{10}$ cycloalkylalkylsulfonyl, $C_2$-$C_8$ alkenylthio, $C_2$-$C_8$ alkenylsulfinyl, $C_2$-$C_8$ alkenylsulfonyl, $C_2$-$C_8$ alkynylthio, $C_2$-$C_8$ alkynylsulfinyl or $C_2$-$C_8$ alkynylsulfonyl; and each q is independently 0, 1, or 2.

In some further embodiments, the reducing agent comprises a borohydride reducing agent selected from sodium borohydride ($NaBH_4$), sodium triacetoxyborohydride ($NaBH(CH_3COO)_3$), lithium borohydride ($LiBH_4$), potassium borohydride ($KBH_4$), sodium cyanoborohydride ($NaB(CN)H_3$), tetramethylammonium borohydride ($(CH_3)_4NBH_4$), tetraethylammonium borohydride ($(C_2H_5)_4NBH_4$), borane ($BH_3$), diborane ($B_2H_6$), bis-3-methyl-2-butylborane ($[(CH_3)_2CHCH(CH_3)]2BH$) or mixtures thereof. In some further embodiments, the reducing agent comprises lithium aluminium hydride ($LiAlH_4$), diisobutylaluminium hydride (DIBALH), lithium tri-tert-butoxyaluminum hydride ($LiAlH[OC(CH_3)_3]_3$), lithium tri-methoxyaluminum hydride ($LiAlH(OCH_3)_3$), or mixtures thereof. In some embodiments, the reducing agent comprises hydrogen in conjunction with a metal catalyst including, for example, Raney nickel, supported palladium, supported platinum, or mixtures thereof.

In some embodiment, the invention also relates to a method for preparing a compound of Formula 7

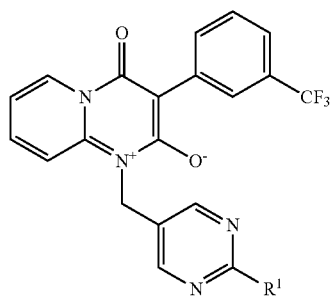

Formula 7 wherein $R^1$ is H or $C_1$-$C_3$ alkyl,
comprising contacting a compound of Formula 1 with the compound (8),

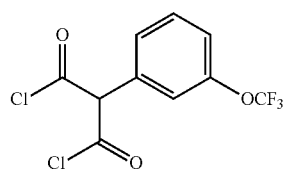

Formula 8 wherein the compound of Formula 1 is prepared by the methods described herein.

This invention also relates to a compound of Formula 4 and/or Formula 5

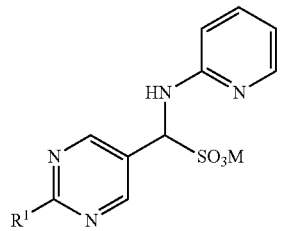

Formula 4

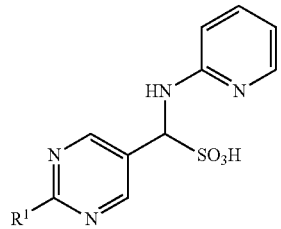

Formula 5 wherein $R^1$ is H or $C_1$-$C_3$ alkyl and M is Na or K or Li.

This invention also relates to a compound of Formula 6

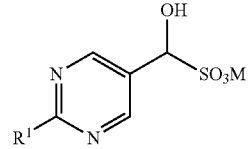

Formula 6 wherein $R^1$ is H or $C_1$-$C_3$ alkyl and M is Na or K or Li.

DETAILED DESCRIPTION OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process, method, article, or apparatus that comprises a list of elements is not necessarily limited to only those elements but may include other elements not expressly listed or inherent to such composition, mixture, process, method, article, or apparatus.

The transitional phrase "consisting of" excludes any element, step, or ingredient not specified. If in the claim, such phrase would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

Where applicants have defined an invention or a portion thereof with an open-ended term such as "comprising," it should be readily understood that (unless otherwise stated) the description should be interpreted to also describe such an invention using the terms "consisting essentially of" or "consisting of"

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "ambient temperature" or "room temperature" as used in this disclosure refers to a temperature between about 18° C. and about 28° C.

In the above recitations, the term "alkyl", includes straight-chain or branched alkyl, such as, methyl, ethyl, n-propyl, i-propyl, or the different butyl isomers. As used herein, haloalkanes are alkanes partially or fully substituted with halogen atoms (fluorine, chlorine, bromine or iodine). Examples of haloalkanes include $CH_2Cl_2$, $C_1CH_2CH_2C_1$, $C_1CH_2CH_2CH_2CH_3$, and $CCl_3CH_3$. Halogenated benzenes are benzenes partially or fully substituted with halogen atoms (fluorine, chlorine, bromine or iodine). Examples of halogenated benzenes include chlorobenzene, 1,2-dichlorobenzene and bromobenzene. $C_7$-$C_{10}$ aromatic hydrocarbons are compounds containing one benzene ring which is substituted with alkyl groups. Examples of $C_7$-$C_{10}$ aromatic hydrocarbons include toluene, xylenes, ethyl benzene and cumene (iso-propylbenzene). $C_5$-$C_{10}$ aliphatic hydrocarbons are straight-chain or branched hydrocarbons. Examples of $C_5$-$C_{10}$ aliphatic hydrocarbons include n-hexane, mixed hexanes, n-heptane and mixed heptanes. $C_5$-$C_{10}$ cycloaliphatic hydrocarbons are cyclic hydrocarbons that can be substituted with straight-chain or branched alkyl groups. Examples of $C_5$-$C_{10}$ cycloaliphatic hydrocarbons include cyclopentane, methylcyclopentane, cyclohexane and methylcyclohexane.

Bisulfite salts and metabisulfite salts are well known in the art. Examples of bisulfite salts include sodium bisulfite, potassium bisulfite, and ammonium bisulfite. Examples of metabisulfite salts include sodium metabisulfite, potassium metabisulfite, and ammonium metabisulfite.

Embodiments of the present invention include:

Embodiment 1. A method of preparing a compound of Formula 1

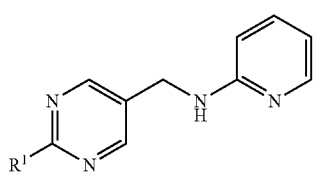

Formula 1 wherein $R^1$ is H, comprising:
(A) contacting a compound of Formula 2 or Formula 2a

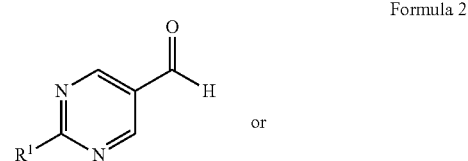

Formula 2 or

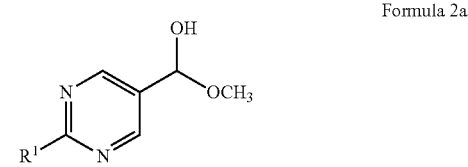

Formula 2a wherein $R^1$ is H,
with 2-aminopyridine (3)

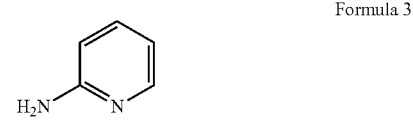

Formula 3 and a salt consisting of a bisulfite salt, a metabisulfite salt, or a mixture of a bisulfite salt and a metabisulfite salt, in the presence of a solvent S1 consisting of water or a mixture of water and an alcohol, to form a col-Ian/mind of Formula 4

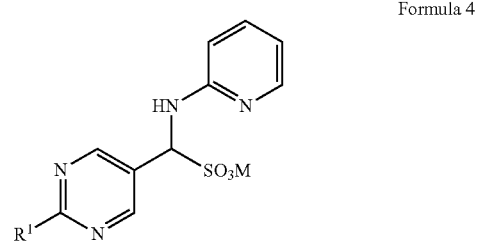

Formula 4 wherein $R^1$ is H and M is an inorganic or organic cation;
(B) contacting the compound of Formula 4 with an inorganic or organic acid in the presence of a solvent S2 consisting of water or a mixture of water and an alcohol to form a compound of Formula 5

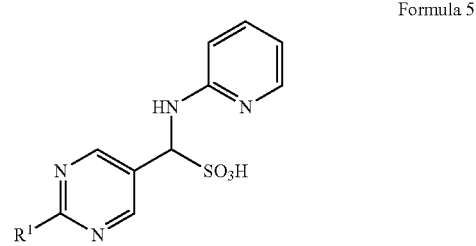

Formula 5 wherein $R^1$ is H; and
(C) contacting the compound of Formula 4 or Formula 5 with a borohydride reducing agent in the optional presence of an inorganic or organic base and a solvent S3 consisting of an alcohol or a mixture of water and an alcohol to form the compound of Formula 1.

Embodiment 2. The method of Embodiment 1 wherein the salt in Step A is a bisulfite salt.

Embodiment 2a. The method of Embodiment 2 wherein the salt in Step A is sodium bisulfite, potassium bisulfite or ammonium bisulfite.

Embodiment 2b. The method of Embodiment 2a wherein the salt in Step A is sodium bisulfite.

Embodiment 3. The method of Embodiment 1 wherein the salt in Step A is a metabisulfite salt.

Embodiment 3a. The method of Embodiment 3 wherein the salt in Step A is sodium metabisulfite, potassium metabisulfite or ammonium metabisulfite.

Embodiment 3b. The method of Embodiment 3a wherein the salt in Step A is sodium metabisulfite.

Embodiment 4. The method of any one of Embodiments 1 through 3b wherein the solvent 51 in Step A is water.

Embodiment 4a. The method of any one of Embodiments 1 through 3b wherein the solvent 51 in Step A is a $C_1$-$C_4$ alcohol.

Embodiment 4b. The method of any one of Embodiments 1 through 3b wherein the solvent 51 in Step A is a mixture of water and a $C_1$-$C_4$ alcohol.

Embodiment 4c The method of Embodiment 4b wherein the solvent S1 in Step A is a mixture of water and methanol.

Embodiment 5. The method of Embodiment 1 wherein the inorganic or organic acid in Step B is an inorganic acid.

Embodiment 5a. The method of Embodiment 5 wherein the inorganic acid is hydrochloric acid, sulfuric acid or phosphoric acid.

Embodiment 5b. The method of Embodiment 5a wherein the inorganic acid is hydrochloric acid.

Embodiment 6. The method of Embodiment 1 wherein the inorganic or organic acid in Step A is an organic acid.

Embodiment 6a. The method of Embodiment 6 wherein the organic acid is formic acid, acetic acid or propionic acid.

Embodiment 6b. The method of Embodiment 6a wherein the organic acid is acetic acid.

Embodiment 7. The method of Embodiment 1 wherein the borohydride reducing agent in Step C is sodium borohydride, lithium borohydride or potassium borohydride.

Embodiment 8. The method of Embodiment 7 wherein the borohydride reducing agent is used in an amount of between 0.30 and 0.70 molar equivalents of the borohydride reducing agent relative to the amount of the compound of Formula 2 used in Step A.

In some embodiments, the aldehyde of formula 2 can be present as its hemi-acetal in methanol as represented as Formula 2a.

Embodiment 9. The method of Embodiment 8 wherein the borohydride reducing agent in Step C is sodium borohydride.

Embodiment 10. The method of Embodiment 1 wherein the inorganic or organic base in Step C is an inorganic hydroxide.

Embodiment 10a. The method of Embodiment 10 wherein the inorganic hydroxide is sodium hydroxide or potassium hydroxide.

Embodiment 11. The method of Embodiment 1 wherein the inorganic or organic base in Step C is an organic base.

Embodiment 11a. The method of Embodiment 11 wherein the organic base is an alkali metal salt of an alcohol.

Embodiment 11b. The method of Embodiment 11a wherein the alkali metal salt of an alcohol is sodium methoxide, sodium ethoxide, sodium iso-propoxide, sodium n-propoxide, potassium methoxide, potassium ethoxide, potassium 1-propoxide, and potassium 2-propoxide.

Embodiment 11c The method of Embodiment 11b wherein the alkali metal salt of an alcohol is sodium methoxide.

Embodiment 12. The method of Embodiment 1 wherein the solvent S3 in Step C is an alcohol.

Embodiment 12a. The method of Embodiment 12 wherein the solvent S3 is a $C_1$-$C_4$ alcohol.

Embodiment 12b. The method of Embodiment 12a wherein the solvent S3 is methanol.

Embodiment 12c The method of Embodiment 1 wherein the solvent S3 in Step C is water.

Embodiment 12d. The method of Embodiment 1 wherein the solvent S3 in Step C is a mixture of water and a $C_1$-$C_4$ alcohol.

Embodiment 12e. The method of Embodiment 12d wherein the solvent S3 is a mixture of water and methanol.

Embodiment 13. The method of Embodiment 1 wherein the reaction time of Step C is between 1 and 6 hours.

Embodiment 14. The method of Embodiment 1 wherein the solvent S1 in Step A is the same as the solvent S2 in Step B.

Embodiment 15. A method for preparing a compound of Formula 7

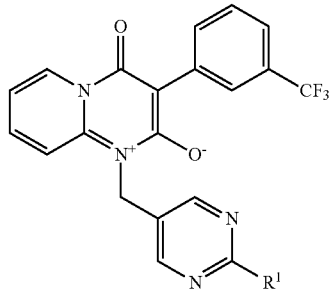

Formula 7 wherein $R^1$ is H or $C_1$-$C_3$ alkyl, comprising contacting a compound of Formula 1 of claim 1 with the compound (8),

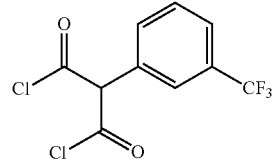

Formula 8 wherein the compound of Formula 1 is prepared by the method of claim 1.

Embodiment 16. The method Embodiment 15 wherein $R^1$ is H.

Embodiment 17. A compound of Formula 4

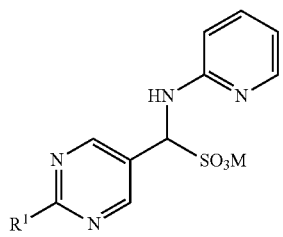
Formula 4 wherein $R^1$ is H and M is sodium or potassium or lithium.

Embodiment 18. A compound of Formula 5

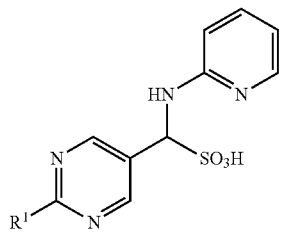
Formula 5 wherein $R^1$ is H.

Embodiment 19. A method for preparing a compound of Formula 1

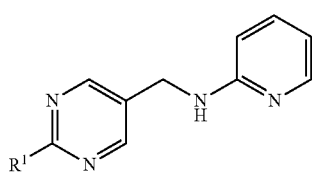
Formula 1 wherein $R^1$ is H,
comprising:
(A1) contacting a compound of Formula 2 or Formula 2a

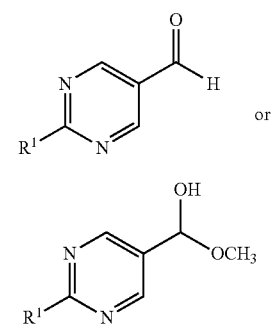
Formula 2
or
Formula 2a wherein $R^1$ is H,
with a salt consisting of a bisulfite salt, a metabisulfite salt, or a mixture of a bisulfite salt and a metabisulfite salt, in the presence of a solvent S1 consisting of water or a mixture of water and an alcohol, to form a compound of Formula 6

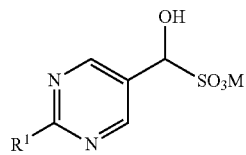
Formula 6 wherein $R^1$ is H and M is an inorganic or organic cation;

(A2) contacting the compound of Formula 6 with 2-aminopyridine (3)

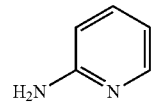
Formula 3 in the presence of a solvent S1 consisting of water or a mixture of water and an alcohol, to form a compound of Formula 4

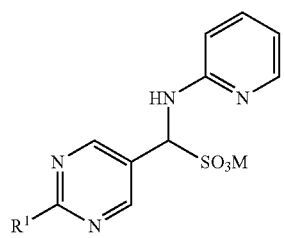
Formula 4 wherein $R^1$ is H and M is an inorganic or organic cation;

(B) contacting the compound of Formula 4 with an inorganic or organic acid in the presence of a solvent S2 consisting of water or a mixture of water and an alcohol to form a compound of Formula 5

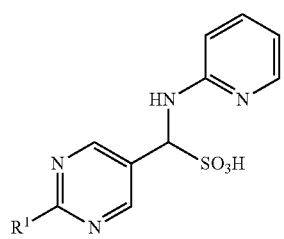
Formula 5 wherein $R^1$ is H; and (C) contacting the compound of Formula 4 or Formula 5 with a borohydride reducing agent in the optional presence of an inorganic or organic base and a solvent S3 consisting of an alcohol or a mixture of water and an alcohol to form the compound of Formula 1.

Embodiment 20. A compound of Formula 6

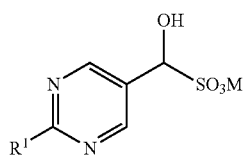

Formula 6 wherein $R^1$ is H and M is sodium or potassium or lithium.

Embodiments of this invention, including Embodiments 1-20 above as well as any other embodiments described herein, can be combined in any manner, and the descriptions of variables in the embodiments pertain not only to the aforedescribed method for preparing the compound of Formulae 1 and 7, but also to the starting compounds and intermediate compounds useful for preparing the compound of Formulae 1 and 7 by this method.

In the following Schemes, the definition of $R^1$ in the compounds of Formulae 1, 2, 4, 5, 6 and 7 is defined herein in the Summary of the Invention and description of Embodiments unless otherwise indicated.

In Step A of the method of the invention, a compound of Formula 4 is prepared by treatment of a compound of Formula 2 with 2-aminopyridine (3) and a bisulfite salt, a metabisulfite salt, or a mixture of a bisulfite salt and a metabisulfite salt, in the presence of an inert solvent S1 or a mixture of inert solvents S1, with optional distillation of solvent as shown in Scheme 1.

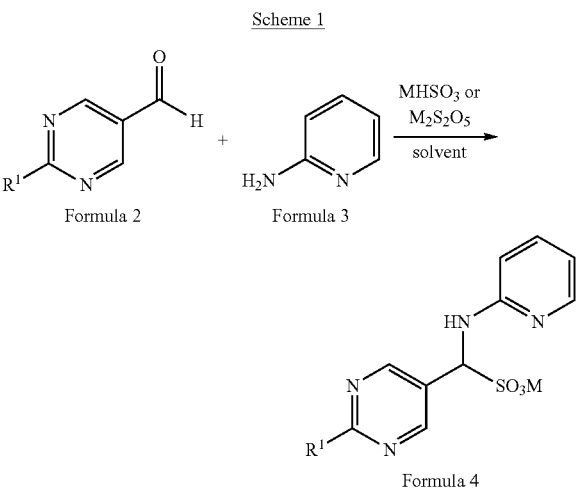

Examples of bisulfite salts include sodium bisulfite, potassium bisulfite, and ammonium bisulfite. Examples of metabisulfite salts include sodium metabisulfite, potassium metabisulfite, and ammonium metabisulfite.

Examples of alcohols suitable for use in Step A include the $C_1$-$C_4$ alcohols such as methanol, ethanol, 1-propanol, 2-propanol, 1-butanol, 2-butanol, 2-methyl-1-propanol, and 2-methyl-2-propanol.

In compounds of Formula 4 the inorganic or organic cation M will correspond to the cation or cations present in the bisulfite and/or metabisulfite salts employed in Step A.

The choice of reaction temperature, reaction pressure, and reaction time of the process of Step A is dependent on the reaction solvent. The process of Step A is conveniently carried out at or below the normal boiling point of the reaction solvent preferably at about 20° C. to about 70° C. and more preferably at about 30° C. to about 60° C. Depending of the solvent employed, the reaction can be carried out at pressures above or below atmospheric pressure. The reaction time will depend on the desired level of conversion and the choice of solvent. Typical reaction times range from 1 to 24 hours.

An alternate synthesis of compounds of Formula 4, comprises a two step procedure in which a compound of Formula 2 is converted to the bisulfite addition compound of Formula 6 (Step A1) which is then treated with 2-aminopyridine (3) to give a compound of Formula 4 (Step A2) as shown in Schemes 1A and 1B.

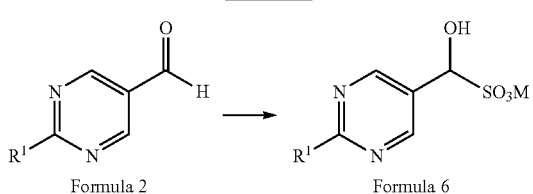

In Step A1 of the method of the invention, a compound of Formula 6 is prepared by treatment of a compound of Formula 2 with a bisulfite salt, a metabisulfite salt, or a mixture of a bisulfite salt and a metabisulfite salt, in the presence of an solvent S1 or a mixture of solvents S1, with optional distillation of solvent as shown in Scheme 1A.

The choice of reaction temperature, reaction pressure, and reaction time of the process of Step A1 is dependent on the reaction solvent. The process of Step A1 is conveniently carried out at or below the normal boiling point of the reaction solvent preferably at about 20° C. to about 70° C. and more preferably at about 20° C. to about 50° C. Depending of the solvent employed, the reaction can be carried out at pressures above or below atmospheric pressure. The reaction time will depend on the desired level of conversion and the choice of solvent. Typical reaction times range from 1 to 24 hours.

It will be understood by those skilled in the art that, in the processes of Scheme 1 and Scheme 1A, the bisulfite salt can be generated in situ by adding a base and sulfur dioxide ($SO_2$) in place of the bisulfite or metabisulfite salt. For example, a compound of Formula 4 could be prepared by treatment of a mixture of a compound of Formula 2, 2-aminopyridine (3), and a base in the presence of a solvent S1 or a mixture of solvents S1 with sulfur dioxide. In the same way, a compound of Formula 6 could be prepared by treatment of a mixture of a compound of Formula 2 and a base in the presence of a solvent S1 or a mixture of solvents S1 with sulfur dioxide.

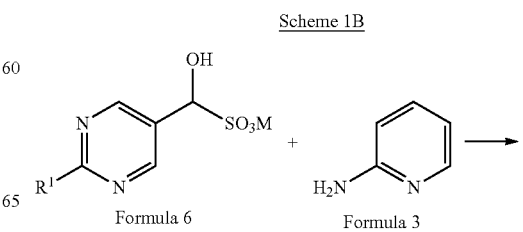

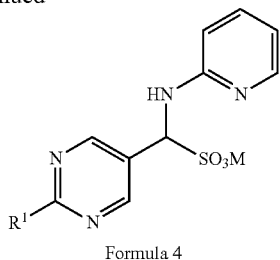

Formula 4

In Step A2 of the method of the invention, a compound of Formula 4 is prepared by treatment of a compound of Formula 6 with 2-aminopyridine (3) in the presence of an solvent S1 or a mixture of solvents S1, with optional distillation of solvent as shown in Scheme 1B.

The choice of reaction temperature, reaction pressure, and reaction time of the process of Step A2 is dependent on the reaction solvent. The process of Step A2 is conveniently carried out at or below the normal boiling point of the reaction solvent preferably at about 20° C. to about 70° C. and more preferably at about 30° C. to about 60° C. Depending of the solvent employed, the reaction can be carried out at pressures above or below atmospheric pressure. The reaction time will depend on the desired level of conversion and the choice of solvent. Typical reaction times range from 1 to 24 hours.

In Step B of the method of the invention, a compound of Formula 5 is prepared by treatment of a compound of Formula 4 with a protic acid as shown in Scheme 2 in the presence of a solvent S2.

Scheme 2

Examples of acids suitable for use in Step (B) include mineral acids such as hydrochloric acid and sulfuric acid, other inorganic acids such as phosphoric acid, organic acids such as formic acid, acetic acid and propionic acid, and sulfonic acids such as para-toluenesulfonic acid, toluenesulfonic acid as a mixture of isomers, and methanesulfonic acid.

In Step C of the method of the invention, a compound of Formula 1 is prepared by treatment of a compound of Formula 4 or Formula 5 with a borohydride reducing agent in the presence of an inert solvent S3 and the optional presence of a base as shown in Scheme 3. Borohydride reducing agents which can be used in Step C of this method include, but are not limited to, sodium borohydride, lithium borohydride, potassium borohydride, sodium triacetoxyborohydride and sodium trimethoxyborohydride. In an embodiment of Step C, the borohydride reducing agent is sodium borohydride.

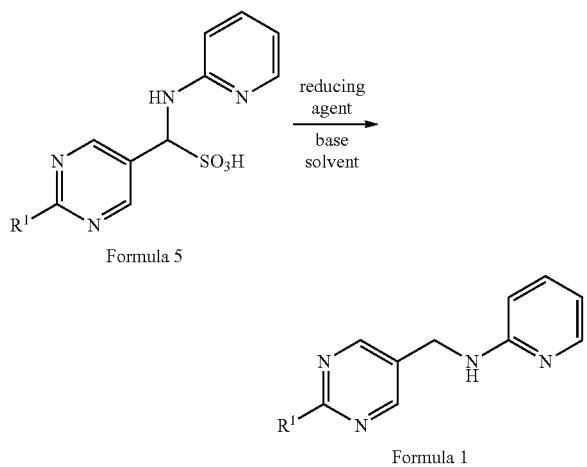

Scheme 3

In instances when the borohydride reducing agent is sodium triacetoxyborohydride or sodium trimethoxyborohydride, it is typical to use 1.0 to 1.5 molar equivalents of the borohydride reducing agent relative to the amount of the compound of Formula 2 charged in Step A. In instances when the borohydride reducing agent is sodium borohydride, lithium borohydride or potassium borohydride, typically 0.25 to 1.0 molar equivalents of the borohydride reducing agent relative to the amount of the compound of Formula 2 of Step A can be used. In an embodiment of Step C, the borohydride reducing agent is sodium borohydride, lithium borohydride or potassium borohydride, and is used in an amount of between 0.30 and 0.70 molar equivalents of the borohydride reducing agent relative to the amount of the compound of Formula 2 of Step A.

In instances in which the compound of Formula 4 is prepared by the process of Scheme 1B, the reaction of Scheme 1B can be carried out in the presence of a borohydride reducing agent to directly produce the compound of Formula 1.

Examples of bases suitable for use in Step (C) include inorganic hydroxides, such as sodium hydroxide and potassium hydroxide, organic bases such as the alkali metal salts of alcohols, examples of which include sodium methoxide, sodium ethoxide, sodium iso-propoxide, sodium n-propoxide, potassium methoxide, potassium ethoxide, potassium 1-propoxide, and potassium 2-propoxide, and amine bases such as ammonia, monoalkylamines such as methylamine and ethylamine, dialkylamines such as dimethyl amine and triethylamine, trialkylamines such as trimethylamine and triethylamine, and aromatic amines such as pyridine.

The solvent S3 is an alcohol, preferably an aliphatic alcohol and more preferably a $C_1$-$C_4$ alcohol, or water. Alcohol water mixtures in any proportion may also be used as the solvent. The alcohol, water, or mixed alcohol and water solvent may be used as mixtures with other solvents including (a) $C_7$-$C_{10}$ aromatic hydrocarbons (for example, toluene, xylenes (as the pure ortho, meta and para isomers, as mixtures thereof, or as mixtures with ethylbenzene), ethyl benzene and cumene (iso-propylbenzene)), (b) halogenated benzenes (for example, chlorobenzene and 1,2-dichlorobenzene), (c) haloalkanes (for example, dichloromethane, 1,2-dichloroethane and 1-chlorobutane), and (d) ethers (for example, tetrahydrofuran, 2-methyltetrahydrofuran, tert-butyl methyl ether, and dioxane).

The reaction temperature in Step C of this method typically ranges from −10 to 50° C. In one embodiment of Step C, the reaction temperature ranges from 0 to 30° C. In another embodiment of Step C, the reaction temperature ranges from 5 to 15° C. The reaction time in Step C of this method typically ranges from 1 hour to greater than 24 hours. In an embodiment of Step C, the reaction time is between 1 and 6 hours.

In an embodiment of this invention, the alcohol solvent used in Step A either alone or in combination with water is the same alcohol solvent used in the subsequent steps and is selected from methanol, ethanol, 1-propanol, 2-propanol, 1-butanol, 2-butanol, 2-methyl-1-propanol, and 2-methyl-2-propanol. In an embodiment of this invention, the alcohol solvents 51, S2 and S3 is methanol alone or in combination with water. In a further embodiment of this invention, the solvent 51 is methanol water, the solvent S2 is methanol water, and the solvent S3 is methanol.

The compound of Formula 1 can be isolated from the reaction mixture of Step C by standard techniques known in the art for the isolation of products from reduction reactions. When a borohydride reducing agent is used, typically water is added to the reaction mixture or the reaction mixture is added to water to dissolve and/or digest boron complexes and/or any remaining borohydride reagent. The pH of the aqueous phase can optionally be raised by the addition of a base or lowered by the addition of an acid to facilitate digestion of any residual borohydride reagent and intermediate boron complexes. Suitable bases include alkali metal hydroxides, carbonates and bicarbonates. Suitable acids include mineral acids such as hydrochloric acid, sulfuric acid, and phosphoric acid and organic acids such as acetic acid.

Once the boron complexes and/or any remaining borohydride reagent are digested, the compound of Formula 1 can be extracted from this aqueous phase using a water immiscible organic solvent S4. Depending on the amount of water and alcohol solvent employed it may be advantageous to remove the excess alcohol solvent by distillation prior to extraction.

In some cases the crude product may include extractable non-basic impurities which can be separated by an initial extraction at low pH. In such cases, adjusting the pH of the aqueous phase to pH 5 or less minimizes loss of the product of Formula 1 to the organic phase, since at pH 5 or less, the compound of Formula 1 will partition into the aqueous layer. Once the non-basic impurities are extracted, the compound of Formula 1 can be isolated by adjusting the pH to 5 or greater followed by extraction from the aqueous phase into a water immiscible organic solvent. The ease of extraction of the compound of Formula 1 from the aqueous phase will be dependent on factors such as the pH of the aqueous phase, the amount of water charged relative the amount of the compound of Formula 1, and the solvent selected for the extraction. It is often advantageous at this point to maintain the pH of the aqueous phase at about 5 to 7 during the extraction to facilitate extraction of the compound of Formula 1 while suppressing the extraction of more basic process impurities. Thus, the pH of the aqueous phase is adjusted with aqueous base to pH 5 or greater, and the compound of Formula 1 is extracted into an organic solvent S4. Typical organic solvents S4 include $C_7$-$C_{10}$ aromatic hydrocarbons, haloalkanes, halogenated benzenes, $C_5$-$C_{10}$ aliphatic hydrocarbons, and $C_5$-$C_{10}$ cycloaliphatic hydrocarbons. In one embodiment, the organic solvent S4 is toluene, dichloromethane, 1,2-dichloroethane or 1-chlorobutane.

In an embodiment of this method, Step (C) further comprises (i) contacting the reaction mixture with water and adjusting the pH of the reaction mixture with acid to pH less than 5, (ii) removing alcohol solvent by distillation, (iii) extracting non-basic impurities, (iv) adjusting the pH of the aqueous phase to pH 5 or greater with an aqueous base, and (v) extracting the compound of Formula 1 from the aqueous phase into an organic solvent S4. In a further embodiment, the pH of the aqueous phase in (iv) above is adjusted with aqueous base to between pH 5 and 7. In a further embodiment, the pH of the aqueous phase in (iv) above is adjusted with aqueous base to between pH 5 and 6.

If the compound of Formula 1 is a solid at ambient temperature, it can be isolated from the organic layer and organic extracts by solvent exchange into a suitable crystallization solvent. Subsequent cooling of the crystallization solvent, isolation of the solid product by filtration, and optional washing of the product with an appropriate organic solvent provides the purified compound of Formula 1.

Compounds of Formula 1 can be coupled with the compound (8) to provide the compounds of Formula 7 as shown in Scheme 4; such a coupling method is described in PCT Patent Application Publication WO 2013/090547. When $R^1$ in Formula 7 is H, the resulting compound is the insecticide triflumezopyrim (2,4-dioxo-1-(5-pyrimidinylmethyl)-3-[3-(trifluoromethyl)phenyl]-2H-pyrido[1,2-c]pyrimidinium inner salt, CAS Registry No. 1263133-33-0). Triflumezopyrim is described in PCT Patent Application Publications WO 2011/017351 and WO 2012/092115.

The present method of preparing the compounds of Formula 1 thus can be used in the preparation of insecticidally active compounds of Formula 7.

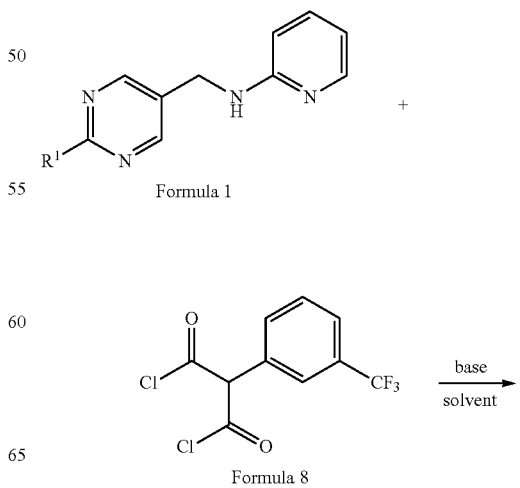

Scheme 4

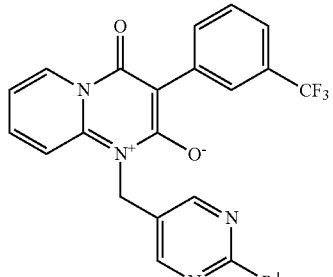

Formula 7

In the following Examples, Proton-NMR analysis was performed on a Bruker Avance III HD 400 MHz instrument or a Bruker Avance III 500 MHz instrument. $^1$H NMR spectra are reported in ppm downfield from tetramethylsilane; "s" means singlet, "d" means doublet, "b" means broad, "br d" means broad doublet, "dd" means doublet of doublets, "br t" means broad triplet, "dt" means doublet of triplites, and "m" means multiplet.

High pressure liquid chromatograph (HPLC) analysis was performed using a Hewlett Packard Series 1290 Infinity II instrument equipped with a diode array UV detector (monitored at 215 nm) and fitted with a Zorbax Eclipse XDB C18 (150 mm×4.6 mm×5 μm) column. The column was maintained at 25° C. and the flow rate was 1 mL per minute. The mobile phase was composed of 10 mM ammonium bicarbonate in water (A) and acetonitrile (B). The mobile phase program was 85% A:15% B for 12 minutes, changed to 40% A:60% B over 4 minutes, and then changed to 20% A:80% B over four minutes.

Preparation Example 1

Synthesis of N-[(5-pyrimidinyl)methyl]-2-pyridinamine

Step A: Preparation of Sodium (2-pyridylamino)-pyrimidin-5-yl-methanesulfonate

To a 2 L round bottomed flask were added 687.7 g of a 2.52 wt % solution of 5-pyrimidinecarboxaldehyde in methanol (17.3 g, 0.16 mole contained 5-pyrimidinecarboxaldehyde), 108.4 g of a 17 wt % solution of sodium bisulfite in water (18.4 g, 0.176 mol contained sodium bisulfite), and 18.1 g of a 99 wt % of 2-aminopyridine (0.192 mole). The reaction mixture was then concentrated under the reduced pressure (110-200 mmHg) via rotary evaporator at 50° C. bath temperature until most of methanol was distilled off. The resulting suspension was transferred to a 200 mL jacketed resin kettle equipped with an overhead stirrer, a thermocouple, and a recirculating heating. The flask was rinsed with 30 mL of water, which was then combined with the reaction mixture. The resulting suspension was heated to 60° C. for 2 hours. HPLC analysis of the reaction mixture indicated 70-75 area % sodium (2-pyridylamino)-pyrimidin-5-yl-methanesulfonate. The product separated as a gum. A small sample of this was removed and analyzed by NMR. $^1$H NMR (400 MHz, DMSO-d$_6$) δ 9.02 (s, 1H), 8.87 (s, 2H), 7.92 (m, 1H), 7.52 (b, 1H), 7.44 (m, 1H), 6.87 (d, J=8.5 Hz, 1H), 6.54 (m, 1H), 5.92 (d, J=9.2 Hz, 1H).

Step B: Preparation of (2-Pyridylamino)-pyrimidin-5-yl-methanesulfonic Acid

The reaction mixture from Step A was cooled to 15° C. and acidified to pH 4 with concentrated HCl (35%, ~16 mL). The resulting slurry was stirred at 10° C. for 1 hour. The solid was then collected by filtration, washed with 100 mL of cold water, and dried at room temperature to afford 36 g of product. Analysis of the product by NMR with internal standard indicated 93.8 wt % (HPLC 99.5 area %) (2-pyridylamino)-pyrimidin-5-yl-methanesulfonic acid (79% yield from pyrimidine-5-carboxaldehyde). $^1$H NMR (400 MHz, DMSO-d$_6$) δ 9.50 (b, 1H), 9.15 (s, 1H), 8.95 (s, 2H), 8.05 (dd, J=1.0, 6.3 Hz, 1H), 7.98 (m, 1H), 7.34 (d, J=9.0 Hz, 1H), 6.98 (m, 1H), 5.91 (d, J=9.5 Hz, 1H). M.P. 182° C.

Step C: Preparation of N-[(5-pyrimidinyl)methyl]-2-pyridinamine

To a 200 mL jacketed resin kettle equipped with an overhead stirrer, a thermocouple, a recirculating heating and cooling bath, and a nitrogen inlet was added 30.0 g of 94.1 wt % (2-pyridylamino)-pyrimidin-5-yl-methanesulfonic acid (0.106 mol) followed by 120 mL of methanol. The resulting slurry was then cooled down to 15° C., and 22.9 g of 25 wt % sodium methoxide in methanol (0.106 mol) was added slowly to yield a yellowish orange suspension. In a 100 mL erlenmeyer flask, 2.01 g of 98% sodium borohydride powder (0.053 mol) was dissolved in 22.9 g of 25 wt % sodium methoxide in methanol (0.106 mol) and 30 mL of methanol. The resulting borohydride solution was added into the 200 mL jacketed reactor over 10 min while maintaining the temperature of the reaction mixture at 10 to 15° C. The reaction mixture was stirred at 15° C. for about 3 hours, after which time HPLC analysis of the reaction mixture indicated 94.2 area % N-[(5-pyrimidinyl)methyl]-2-pyridinamine. The reaction was then quenched with 65 mL of 6 N HCl solution to achieve pH about 3, and the resulting mixture was stirred at room temperature overnight. Most of the methanol was distilled off under the reduced pressure at 50° C., and the pH of the remaining aqueous layer was adjusted to 6 by the addition of 5.8 mL of 50% NaOH solution. The aqueous layer was then extracted with dichloromethane (5×50 mL), with the periodic addition of 50% NaOH to maintain the pH of the aqueous layer between about 5.8 and 6.0. The combined dichloromethane extracts were concentrated to dryness using a rotary evaporator to give 18.05 g of light yellow solid. The solid was transferred to a 200 mL jacketed resin kettle equipped with overhead stirrer, a thermocouple, a recirculating heating and cooling bath, and a nitrogen inlet, and 30 mL of dichloromethane was added. The resulting light slurry was heated to 35° C. to obtain a homogeneous solution, which then cooled to 12° C. to induce crystallization with seeding. Once crystallization was initiated, 90 mL of heptane was added over 60 min. The mixture was then further cooled to 5° C. over 40 min, and held for one hour, after which time the product was collected by filtration, washed with 30 mL of cold heptane, and dried in a vacuum oven at about 40° C. with a nitrogen bleed to afford 16.8 g of product. Analysis of the product by HPLC indicated 97.5 wt % (98.9 area %)N-[(5-pyrimidinyl) methyl]-2-pyridinamine (83% yield). $^1$H NMR (400 MHz, DMSO-d$_6$) δ 9.06 (s, 1H), 8.77 (s, 2H), 7.98 (m, 1H), 7.42 (m, 1H), 7.2 (br t, 1H), 6.58 (dt, J=0.9, 8.5 Hz, 1H), 6.54 (m, 1H), 4.52 (d, J=5.3 Hz, 2H).

Preparation Example 2

A Second Synthesis of (2-pyridylamino)-pyrimidin-5-yl-methanesulfonic Acid

Step A: Preparation of 5-pyrimidinecarboxaldehyde-sodium Bisulfite Adduct

To a 500 mL round bottom flask were added 150 g of a 3.4 wt % solution of 5-pyrimidinecarboxaldehyde in methanol (5.1 g, 0.047 mole contained 5-pyrimidinecarboxaldehyde) and 20.9 g of a 28.2 wt % solution of sodium bisulfite in water (5.9 g, 0.057 mol contained sodium bisulfite). The resulting solution was then stirred for 30 min at ambient temperature. Most of the methanol was distilled off using a rotary evaporator at 50° C. to give a light slurry, to which 40 mL of isopropyl alcohol was added. The resulting slurry was cooled down to ambient temperature and stirred overnight after which time the product was collected by filtration, washed with 15 mL of mixture of water and isopropyl alcohol (5 and 10 mL), and suction-dried at ambient temperature for 4 hours to give 16.6 g of white solid. Analysis of the product by NMR indicated 61 wt % of 5-pyrimidinecarboxaldehyde-sodium bisulfite adducts (quantitative yield from 5-pyrimidinecarboxaldehyde). $^1$H NMR (500 MHz, DMSO-$d_6$) δ 9.04 (s, 1H), 8.78 (s, 2H), 6.48 (b, 1H), 5.09 (d, J=5.6 Hz, 1H).

Step B: Preparation of Sodium (2-pyridylamino)-pyrimidin-5-yl-methanesulfonate To a 50 mL round bottomed flask were added 2.0 g of a 73 wt % of 5-pyrimidinecarboxaldehyde-sodium bisulfite adduct (6.9 mmole), 0.78 g of a 99 wt % of 2-aminopyridine (8.3 mmole), and 8 mL of water. The resulting mixture was heated to 60° C. for 5 hours. HPLC analysis of the reaction mixture indicated 40-45 area % sodium (2-pyridylamino)-pyrimidin-5-yl-methanesulfonate.

Step C: Preparation of (2-pyridylamino)-pyrimidin-5-yl-methanesulfonic Acid The reaction mixture from Step B was then allowed to cool down to 20° C. and acidified to pH 3 with concentrated HCl (35%). The resulting slurry was stirred at 20° C. for 2 hours. The solid was then collected by filtration, washed with 10 mL of cold water, and dried at room temperature to afford 0.98 g of product. Analysis of the product by NMR with internal standard indicated 95 wt % (HPLC >99 area %) of the title compound (51% yield from 5-pyrimidinecarboxaldehyde-sodium bisulfite adduct).

Preparation Example 3

A Third Synthesis of (2-pyridylamino)-pyrimidin-5-yl-methanesulfonic Acid

Step A: Preparation of Sodium (2-pyridylamino)-pyrimidin-5-yl-methanesulfonate To a 1 L round bottomed flask was added 560.5 g of a 3.2 wt % solution of 5-pyrimidinecarboxaldehyde in methanol (18.3 g, 0.169 mole contained 5-pyrimidinecarboxaldehyde). The solution was concentrated using a rotary evaporator with a bath temperature of 20° C. and a pressure of 50-55 mmHg. After greater 80% of the methanol was removed, the pressure was adjusted to 25-30 mmHg and additional solvent removed to leave 94.3 g of residue. The residue was then transferred to a 500 mL 4-neck jacketed resin kettle (equipped with an overhead stirrer, a thermocouple, a recirculating heating bath, and variable take off distillation head) and rinsed in with three 5 mL portions of the methanol distillate. The reactor was purged with nitrogen and allowed to stand over the weekend under nitrogen. The recirculating bath to the reactor jacket was set to 20° C. and a solution of 19.4 g (0.186 mole) of sodium bisulfite in 97 g of water was then added dropwise over 30 minutes with stirring. The reactor temperature increased from 20.6° C. to 25.0° C. during the first 15 minutes of the addition and dropped to 23.8° C. by the end of the addition.

The resulting thin yellow slurry was stirred for 5 minutes and 19.3 g (0.203 mole) of >99% 2-aminopyridine added in one portion. The 2-aminopyridine dissolved quickly and the temperature dropped from 22.9° C. to 20.2° C. in one minute. The reaction mixture was stirred for about two hours with a jacket temperature of 20° C. and then heated at 49-51° C. for 2 hours and fifty minutes. The pressure of the system was then carefully reduced to 150 mmHg to initiate distillation of solvent. About 25 mL of distillate was collected over 25 minutes. The pressure was lowered to 110 mmHg and distillation continued for another 1 hour and fifty minutes. The total amount of distillate collected up to this point was about 70 mL. Vacuum was broken with nitrogen and the mixture allowed the stand overnight at room temperature under nitrogen. Vacuum distillation was resumed on the following day with a jacket temperature of 55° C. and a pressure of 110 mmHg. The pressure was dropped to 100 mmHg and then to 90 mmHg. Distillation was slow. After an hour at 90 mmHg, a total of ~80 mL of distillate had been collected over two days. Vacuum was broken with nitrogen.

Step B: Preparation of (2-pyridylamino)-pyrimidin-5-yl-methanesulfonic Acid The reaction mixture from Step A was cooled to 13° C. and the pH adjusted to ~4 by the dropwise addition of concentrated HCl (38%, ~20 g) over about 1.6 hours. The reaction mixture was stirred for 1 hour at 10° C., the product collected by filtration, displacement washed with 3 times with water (40 mL, 40 mL and 20 mL) and dried in a vacuum oven overnight at 50° C. under a nitrogen purge to give 35.0 g of product. Analysis of the product by NMR with internal standard indicated 92 wt % (2-pyridylamino)-pyrimidin-5-yl-methanesulfonic acid (71% yield from 5-pyrimidinecarboxaldehyde).

What is claimed is:

1. A compound of Formula 4 and/or Formula 5,

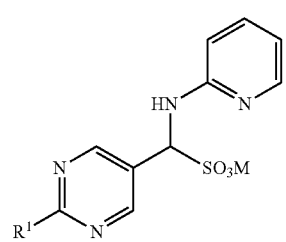

Formula 4

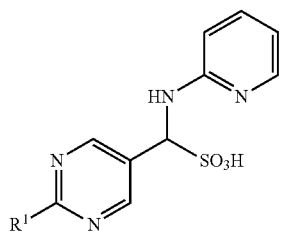
Formula 5
wherein $R^1$ is H or $C_1$-$C_3$ alkyl and M is Na or K or Li.
* * * * *